United States Patent [19]

Kamen

[11] 4,449,976
[45] May 22, 1984

[54] DEVICE FOR PRESERVING CONTINUITY OF INTRAVENOUS FLOW

[75] Inventor: Dean L. Kamen, Bedford, N.H.

[73] Assignee: Baxter Travenol Laboratories, Inc., Deerfield, Ill.

[21] Appl. No.: 319,222

[22] Filed: Nov. 9, 1981

Related U.S. Application Data

[63] Continuation-in-part of Ser. No. 266,072, May 21, 1981.

[51] Int. Cl.³ .............................................. A61M 5/14
[52] U.S. Cl. .................................. 604/254; 604/127; 137/192; 137/399
[58] Field of Search ............ 128/214 R, 214 C, 214.2, 128/274; 137/182, 192, 399; 604/127, 247, 604/251–254

[56] References Cited

U.S. PATENT DOCUMENTS

| | | | |
|---|---|---|---|
| 3,311,268 | 3/1967 | Fields | 128/214 C X |
| 3,738,361 | 6/1973 | Price | 128/214 C X |
| 3,942,526 | 3/1976 | Wilder et al. | 128/214 C X |
| 4,078,563 | 3/1978 | Tuseth | 128/214 C |
| 4,079,743 | 3/1978 | Weston | 137/192 X |
| 4,173,222 | 11/1979 | Muetterties | 128/214 C |

*Primary Examiner*—Dalton L. Truluck
*Attorney, Agent, or Firm*—John A. Caruso; Paul C. Flattery; Bruce D. Sunstein

[57] ABSTRACT

A device for reducing the rate of flow from a reservoir as the reservoir empties requires only a single chamber having an input, for receiving fluid from a reservoir, and an output port. There is a provision for sensing fluid level in the chamber, and a separate provision for reducing the flow through the output port when fluid level in the chamber has fallen to a predetermined level. In a preferred embodiment of the invention, fluid level is sensed by a float, which, after falling to a predetermined level, actuates a plunger that reduces flow through an aperature at the bottom of the chamber.

8 Claims, 3 Drawing Figures

DEVICE FOR PRESERVING CONTINUITY OF INTRAVENOUS FLOW

DESCRIPTION

This application is a continuation in part of my co-pending application Ser. No. 266,072, filed May 21, 1981.

TECHNICAL FIELD

The present invention relates to devices regulating the flow from a reservoir of fluid that is to be transferred intravenously to a patient. More particularly, the invention relates to a device for reducing the flow rate as the reservoir empties.

BACKGROUND ART

A traditional problem in the prior art has been identifying when a fluid reservoir is in an empty or near empty condition. For example, numerous devices, including the device, for example, described in my U.S. Pat. No. 4,137,915, have been developed to control flow rate and to identify the existence of an empty or near-empty condition. If a reservoir has emptied without the knowledge of the medical personnel attending the patient, a number of undesirable effects may result. The medical risks resulting from the absence of flow from the intravenous needle inserted into the patient make common the practice of inserting a new intravenous needle into the patient if additional fluid from a new reservoir is to be introduced to the patient. The introduction of a succession of needles to a patient causes trauma to the patient, and requires extra attention of medical personnel to the patient.

A common prior art approach to this problem has been the use of fluid control devices that include a "keep vein open" ("KVO") mode of operation. In this mode, which is sometimes designated as an "alarm" state, fluid is permitted to enter the patient only at a substantially slower rate than under normal conditions. In this manner, the rate at which the reservoir is emptied is substantially reduced, so as to prolong the period of time before flow stops. Such control devices, however, are typically bulky, expensive, and complicated. Their complexity makes them prone to failure and misuse. Moreover, such devices often require external sources of power.

There is disclosed, in U.S. Pat. No. 4,173,222, issued for an invention of Muetterties, a device that causes flow to revert to a KVO flow rate when the reservoir has emptied. That device, however, involves the use of two drip chambers and the use of systems for eliminating air flow through a passage when the KVO mode has been entered. Consequently, the successful operation of that device is conditioned in part on its success in blocking air flow when it enters the KVO mode.

DISCLOSURE OF INVENTION

The present invention provides a device for reducing the rate of flow from a reservoir as the reservoir empties. The invention requires only a single chamber having an input, for receiving fluid from a reservoir, and an output port. There is a provision for sensing fluid level in the chamber, and a separate provision for reducing the flow through the output port when fluid level in the chamber has fallen to a predetermined level. In a preferred embodiment of the invention, fluid level is sensed by a float, which, after falling to a predetermined level, actuates a plunger that reduces flow through an aperture at the bottom of the chamber.

BRIEF DESCRIPTION OF THE DRAWINGS

These and other objects and features of the invention will be more readily understood by consideration of the following detailed description taken with the accompanying drawings, in which.

DESCRIPTION OF SPECIFIC EMBODIMENTS

Figures 1A, 1B, 1C:
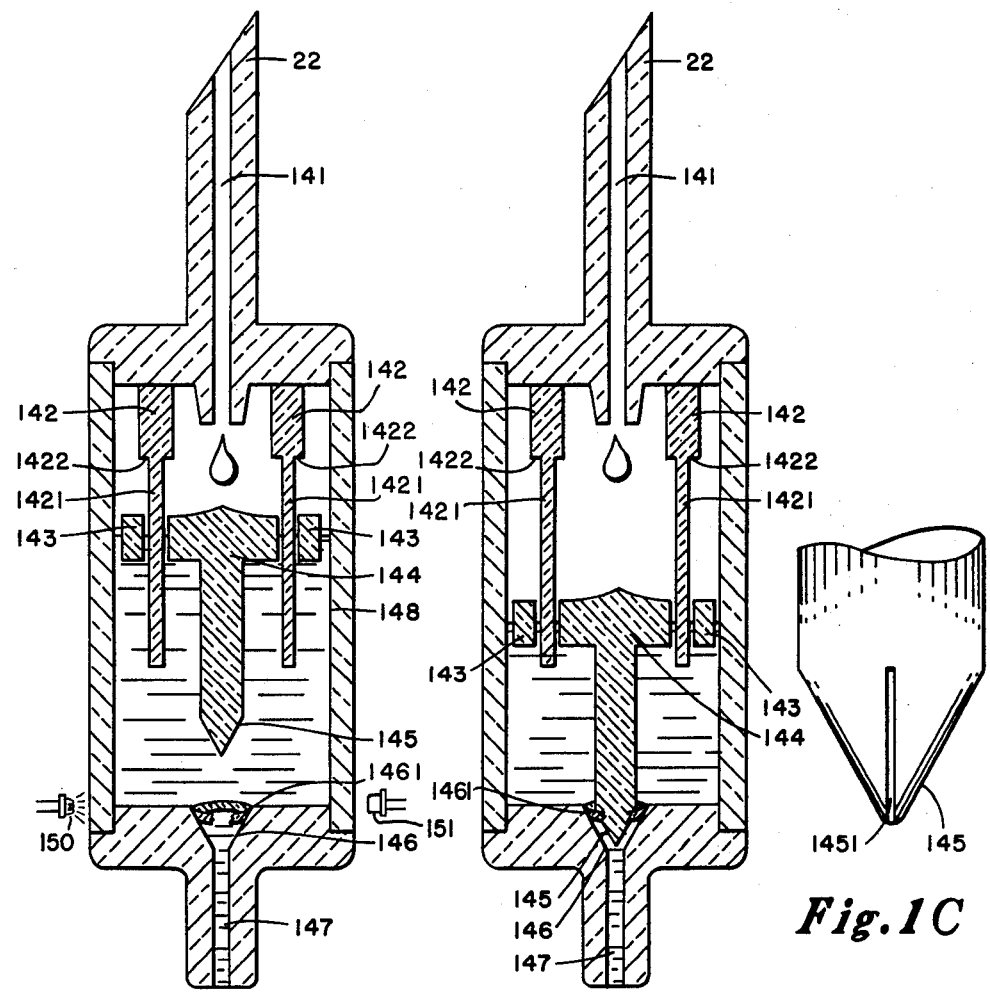
FIG. 1A is a cross section of a preferred embodiment of the present invention.
FIG. 1B is a cross section of the same embodiment as shown in the FIG. 1A with the device in the KVO mode.
FIG. 1C is a detailed view of the plunger end shown in FIGS. 1A and 1B.

In FIG. 1A, there is shown a cross section of a preferred embodiment of the present invention. The device has a chamber formed by interior walls 148 of the housing. The device receives fluid through input 141 when spike or piercing pin 22 is inserted into a reservoir such as an intravenous solution bag. In its normal mode, the device functions as a conventional drip chamber. Fluid that has dripped into the chamber flows through the aperture defined by walls 146 and into the output port 147. Conventional tubing going to other controls, if used, and to the patient can be attached to the base of the device in the vicinity of the output port. The device includes a float 144 that rises and falls with the level of fluid in the chamber. The chamber is cylindrical, and the float is generally disk-shaped. The periphery 143 of the float in this embodiment does not extend to the interior wall 148 of the housing. Fluid entering the chamber from the input 141 therefore drops onto the float 144 and then flows over it and around the periphery 143 downward into the chamber. Flow of drops over the upper float is enhanced by making its upper surface as shown in a cusp shape, so as to reduce splashing of the drops. The float travels vertically on guides 1421 that are affixed on bases 142 to the upper portion of the housing. Upward travel of the float is limited by shoulders 1422. The float 144 includes holes through which the guides 1421 project.

When the reservoir has emptied, fluid level in the chamber will start to fall, and as this happens, float 144 will also fall. As shown in FIG. 1B, when the level has fallen sufficiently, plunger end 145 will become seated against portions of the aperture wall 146. The seal between the plunger end 145 and the aperture wall 146 may be enhanced by use of an O ring 1461. If the seal were perfect, flow from the output port 147 would be totally blocked, a disadvantageous result in most circumstances. Consequently, there is provided, as shown in FIG. 1C, a groove 1451 in plunger end 145. When the plunger end is seated against the aperture wall, the groove 1451 forms a passageway for fluid between the chamber and the output port 147. The effective cross sectional area of the passageway is substantially smaller than the effective cross sectional area at the most constricted part of the fluid path when the plunger end is not seated in the aperture, so that flow rate is reduced when flow is only through the passageway.

The effective cross sectional area of the passageway formed when the device is in the KVO mode is important. The area must be sufficiently large so as to permit fluid flow at a rate sufficient to prevent undesired medical risks resulting from the absence of flow. The area should be sufficiently small, however, to reduce the flow rate when the KVO mode has been entered. It should be pointed out, however, that in the event of the failure of the device to enter the KVO mode, it functions simply as a conventional drip chamber.

It is possible to construct a device in accordance with the present invention whereby the aperture described is sealed completely when KVO mode is entered, and flow is provided through an auxiliary aperture from the chamber housing into the output port. The use of a single aperture as described, however, has the advantage of simplicity.

Thus when fluid in the reservoir is exhausted, the fluid level in the chamber starts to fall until the plunger end 145 is seated in the aperture, and flow is only through the groove 1451. At this point the device has entered the KVO mode, and flow rate is reduced. The device may be provided with a system for signaling when the KVO mode has been entered. Such a signal could be provided using, for example, well-known photoelectric techniques to sense displacement of the float in the chamber as by lamp 150 and sensor 151. Also, although the embodiment described utilizes a groove 1451 in the plunger end 145, a groove could instead, for example, be placed in the aperture wall 146. Other means could also be provided for a constricted flow when the plunger end 145 is seated against the aperture wall 146; for example, the plunger end 145 may be provided with a series of tiny projections or an irregular surface.

In many instances it may be desirable to have the housing transparent so that the float 144 is visible, and the housing may be provided with suitable calibrations to permit rapid visual determination of the height of the float. Finally, in some instances it may be desirable to restrict non-vertical movement of the float and plunger assembly within the chamber by means of a snug fit between the float periphery 143 and housing walls 148; in such a case, the float should be provided with one or more holes to permit communication of fluid between the upper and lower portions of the float and thereby through the chamber to the output port.

Accordingly, while the invention has been described with particular reference to specific embodiments, it will be understood that it may be embodied in a variety of forms diverse from those shown and described without departing from the spirit and scope of the invention as defined by the following claims.

What is claimed is:

1. A device for preserving continuity of fluid flow from a reservoir, such device comprising:

a housing defining a chamber having an input for receiving fluid from the reservoir and an output port;

a float, within the housing, responsive to the fluid level in the chamber;

a mating valve and seat, located in the fluid path between the output port and the chamber;

such valve being mechanically linked to the float, and disposed so as to mate at an area of contact with the seat when the fluid level has fallen to a predetermined level;

such seat being formed as an annular face of the housing and defining an opening to the output port;

at least one of the valve and the seat having a groove on its surface extending entirely across the area of contact, so that when the valve is seated there is permitted flow only at a reduce rate through the groove past the valve to the output port, whereby the flow of fluid abruptly shifts to a reduced rate when the fluid level has fallen to the predetermined level.

2. A device according to claim 1, such device further comprising third means, for restricting non-vertical movement of the plunger within the chamber, so as to preserve orientation of the plunger with respect to the aperture.

3. A device according to claim 2, wherein the float includes a hole and the third means includes a guide, located in the chamber and affixed to the housing, projecting through the hole.

4. A device according to claim 2, wherein the float includes upper and lower portions, means for fluid to communicate between the upper and lower portions, and a periphery shaped so as to fit snugly against the housing and to restrict non-vertical movement of the float and plunger within the chamber.

5. A device according to claim 3, such device further comprising a base on which the guide is mounted, and wherein the base (i) is directly affixed to a part of the housing defining the upper portion of the chamber and (ii) includes a shoulder to limit upward travel of the float in the chamber.

6. A device according to claim 1, wherein the float includes a surface shaped so as to permit rapid and uniform flow of drops of fluid emanating into the chamber from the input.

7. A device according to claim 6, wherein the float includes a cusp, the peak of which is located beneath the input.

8. A device according to claim 1, further comprising signalling means, for signalling when fluid level in the chamber has fallen to the predetermined level.

* * * * *